(12) United States Patent
Stadler et al.

(10) Patent No.: US 6,980,860 B2
(45) Date of Patent: Dec. 27, 2005

(54) DETECTION OF SUPRAVENTRICULAR TACHYCARDIA WITH 1:1 ATRIAL TO VENTRICULAR CONDUCTION

(75) Inventors: Robert W. Stadler, Shoreview, MN (US); Jeffrey M. Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 341 days.

(21) Appl. No.: 10/284,874

(22) Filed: Oct. 31, 2002

(65) Prior Publication Data

US 2004/0088013 A1    May 6, 2004

(51) Int. Cl.[7] .............................................. A61N 1/362
(52) U.S. Cl. ...................................... 607/14; 600/515
(58) Field of Search ............... 607/4–28; 600/515–518

(56) References Cited

U.S. PATENT DOCUMENTS

| | | | | |
|---|---|---|---|---|
| 5,193,550 A | 3/1993 | Duffin | ........................ | 128/697 |
| 5,243,980 A | 9/1993 | Mehra | ........................... | 607/6 |
| 5,312,441 A | 5/1994 | Mader et al. | .................... | 607/5 |
| 5,379,776 A | 1/1995 | Murphy et al. | ............. | 128/705 |
| 5,383,910 A | 1/1995 | den Dulk | ..................... | 607/14 |
| 5,400,795 A | 3/1995 | Murphy et al. | ............. | 128/702 |
| 5,462,060 A | 10/1995 | Jacobson et al. | ........... | 128/702 |
| 6,212,428 B1 | 4/2001 | Hsu et al. | .................... | 600/515 |
| 6,266,554 B1 | 7/2001 | Hsu et al. | .................... | 600/515 |
| 6,275,732 B1 | 8/2001 | Hsu et al. | ..................... | 607/14 |
| 6,393,316 B1 | 5/2002 | Gillberg et al. | ............. | 600/515 |
| 6,438,410 B2 | 8/2002 | Hsu et al. | .................... | 600/516 |
| 6,449,503 B1 | 9/2002 | Hsu | .......................... | 600/518 |
| 6,484,055 B1 | 11/2002 | Marcovecchio | ................ | 607/5 |
| 6,748,269 B2 * | 6/2004 | Thompson et al. | ........... | 607/4 |
| 2002/0019593 A1 | 2/2002 | Hsu et al. | ................... | 600/513 |
| 2002/0032469 A1 | 3/2002 | Marcovecchio | ................ | 607/5 |
| 2002/0087091 A1 | 7/2002 | Koyrakh et al. | ........... | 600/521 |

FOREIGN PATENT DOCUMENTS

EP        1 112 756 A2    7/2001    .......... A61N 1/368

\* cited by examiner

*Primary Examiner*—Scott M. Getzow
(74) *Attorney, Agent, or Firm*—Michael C. Soldner; Girma Wolde-Michael (57) ABSTRACT

The invention is directed to method and process for discriminating supraventricular tachycardia (SVT) with 1:1 atrial to ventricular conduction (AV conduction). Upon detection of a rapid heart rate, an implanted medical device may determine whether the rhythm exhibits insufficient evidence of sinus tachycardia, whether the rhythm exhibits 1:1 conduction, and whether an electrical signal corresponding to the rhythm exhibits a normal morphology. When these tests have been satisfied, the device determines that an SVT with 1:1 AV conduction has been detected.

12 Claims, 4 Drawing Sheets

DETECTION OF SUPRAVENTRICULAR TACHYCARDIA WITH 1:1 ATRIAL TO VENTRICULAR CONDUCTION

TECHNICAL FIELD

The invention relates to processing of cardiac signals, and more particularly, to detection of cardiac arrhythmias.

BACKGROUND

Many implanted cardiac devices monitor the electrical activity of the heart for tachyarrhythmias. An implanted device typically classifies the tachyarrhythmia, i.e., identifies or discriminates the form of tachyarrhythmia. Discrimination is important because some tachyarrhythmias are life threatening and some are not. In addition, the implanted device may apply a therapy to treat the tachyarrhythmia, and discrimination is important to applying an appropriate therapy.

One form of tachyarrhythmia is referred to as supraventricular tachycardia (SVT) with 1:1 atrial to ventricular conduction (AV conduction). SVT with 1:1 AV conduction includes atrioventricular node reentrant tachycardia, atrioventricular reentrant tachycardia (also called Wolff Parkinson White Syndrome), and other atrial tachycardias that may be automatic, triggered, or reentrant.

Some forms of SVTs are referred to as >1:1 AV conduction, meaning that the number of atrial activations exceed the number of ventricular activations. Therapies used to treat 1:1 SVTs may be different from therapies used to treat >1:1 SVTs. Atrial anti-tachycardia pacing, for example, may be relatively safe for treating >1:1 SVTs, but may be more risky for a 1:1 SVT.

SUMMARY

In general, the invention provides method and process for discriminating SVTs with 1:1 AV conduction from other forms of tachyarrhythmia. More specifically, by subjecting a heart rhythm to a series of tests, an implanted medical device may distinguish a 1:1 SVT from other rhythms, and in particular, may distinguish a 1:1 SVT from conditions indicative of a >1:1 SVT.

An implanted medical device may detect a fast heart rhythm by, for example, comparing the interval between successive beats to a threshold. When the time interval between successive beats falls below a threshold time, for example, the heart rate may be deemed to be fast. A fast heart rate, however, does not necessarily indicate the presence of a tachyarrhythmia. A fast heart rate may be due to sinus tachycardia, i.e., a fast heart rate in response to a physiological stimulus, such as exercise.

The implanted medical device may therefore evaluate the heart rhythm for evidence of sinus tachycardia. Typical sinus tachycardia may be indicated by a number of factors, such as a gradual onset of the fast heart rate. The gradual onset of a fast heart rate may be reflected, for example, as a gradual shortening of the time periods between successive R-waves. The implanted medical device may therefore look to whether a shortening of the R-R interval occurred suddenly, rather than gradually. A sudden R-R interval shortening is indicative of tachyarrhythmia, and a gradual R-R interval shortening is evidence of sinus tachycardia. Other changes to the heart rhythm may also be inconsistent with sinus tachycardia, thus indicative of a tachyarrhythmia.

Many forms of tachyarrhythmia, including a 1:1 SVT, may be indicated by a sudden onset of a fast heart rate. To rule out other possible forms of tachyarrhythmia, the implanted medical device may test the heart rhythm for 1:1 atrial to ventricular conduction. If the atrial activation rate generally exceeds the ventricular activation rate, then the implanted device may determine that 1:1 AV conduction is not present and, therefore, neither is a 1:1 SVT.

Some forms of ventricular tachycardia exhibit 1:1 retrograde conduction. These ventricular tachycardias, however, exhibit an abnormal signal morphology of the QRS complex, because the depolarization of the ventricles does not occur by the normal route, i.e., by activation of the His-Purkinje system. Accordingly, the implanted medical device may test the morphology of an electrical signal from the heart to determine whether the morphology is normal, i.e., consistent with normal sinus rhythm. A normal morphology indicates an SVT.

In one embodiment, the invention is directed to a method, comprising sensing a cardiac rhythm, and determining that the cardiac rhythm indicates SVT with 1:1 AV conduction when the rhythm exhibits insufficient evidence of sinus tachycardia, the rhythm exhibits 1:1 conduction, and an electrical signal corresponding to the cardiac rhythm has a normal morphology. In another embodiment, the invention is directed to a computer-readable medium comprising instructions for causing a programmable processor to carry out this method.

In a further embodiment, the invention is directed to a medical device. The medical device includes a sensor proximate to a heart and a processor. The processor senses a cardiac rhythm and an electrical signal corresponding to the cardiac rhythm via the sensor, and determines that the cardiac rhythm indicates an SVT with 1:1 AV conduction when the rhythm exhibits insufficient evidence of sinus tachycardia, the rhythm exhibits 1:1 conduction, and the electrical signal corresponding to the cardiac rhythm exhibits a normal morphology.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
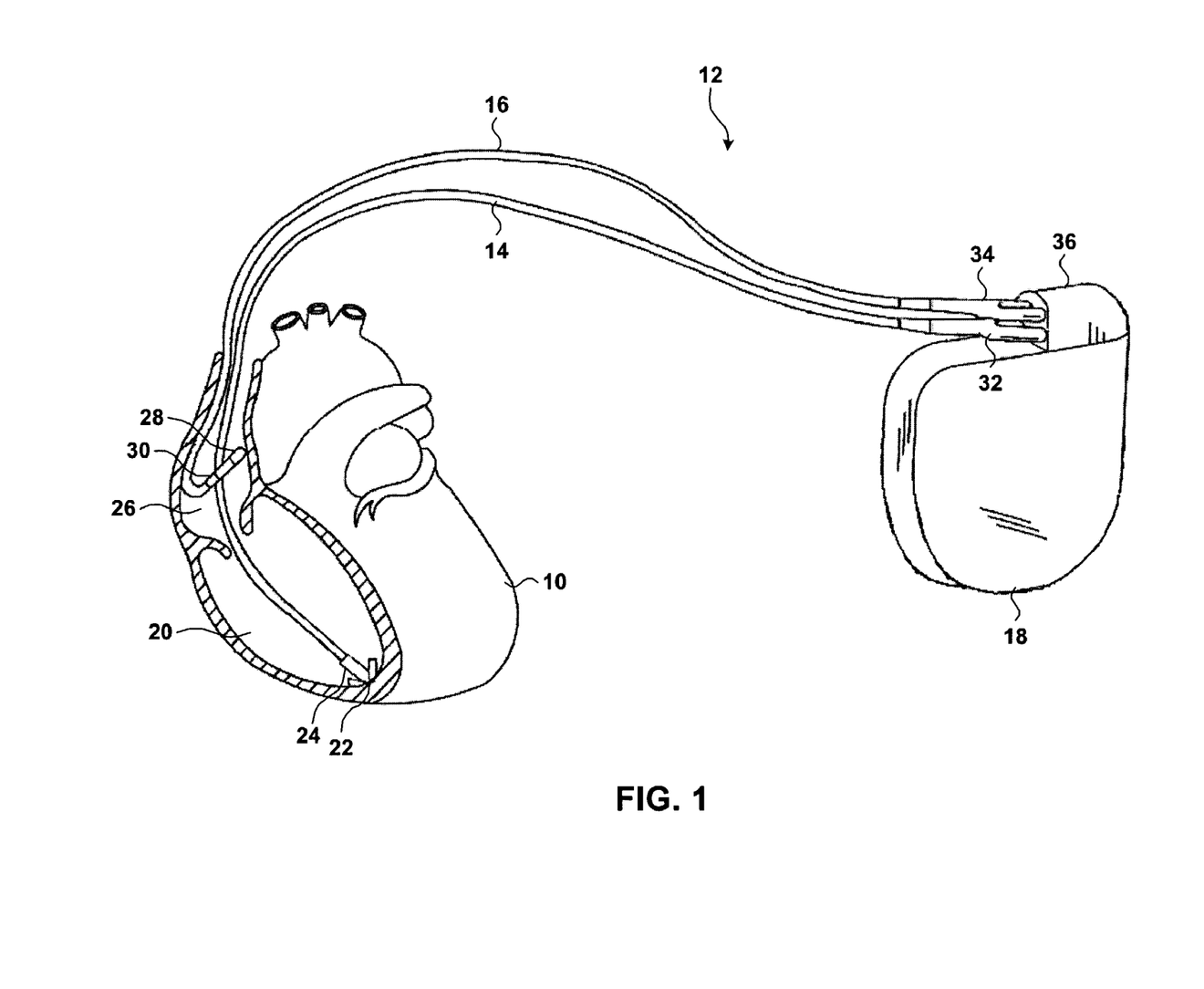
FIG. 1 is a schematic diagram showing an example implanted medical device coupled to a heart of a patient for discriminating SVTs with 1:1 AV conduction.

FIG. 1 shows a human heart 10 with an exemplary implantable medical device ("IMD") 12 that may practice the invention. IMD 12 is a pacemaker comprising a ventricular lead 14 an atrial lead 16. Leads 14 and 16 are attached to a hermetically sealed enclosure 18. Leads 14 and 16 sense electrical signals attendant to the depolarization and re-polarization of heart 10. Leads 14 and 16 may further provide pacing pulses for causing depolarization of cardiac tissue in the vicinity of the distal ends of leads 14 and 16.

FIG. 1 shows ventricular lead 14 disposed in the right ventricle 20 of heart 10. The distal end of lead 14 includes bipolar electrodes 22 and 24, although the invention may be practiced with a unipolar electrode at the distal end of lead 14. Similarly, atrial lead 16 is disposed in the right atrium 26, and includes bipolar electrodes 28 and 30 at the distal end of lead 16, but the invention may be practiced with a unipolar electrode at the distal end of lead 16.

Leads 14 and 16 are coupled to enclosure 18 via connectors 32 and 34, which in turn are coupled to connector module 36. Enclosure 18 includes one or more sense amplifiers that detect atrial and ventricular activations sensed via electrodes 22, 24, 28, 30. By detection of the atrial and ventricular activations, IMD 12 senses a fast cardiac rhythm and determines whether the cardiac rhythm is consistent with an SVT with 1:1 AV conduction. In addition to analyzing the cardiac rhythm, IMD 12 evaluates the morphology of an electrical signal, such as an electrogram, that corresponds to the cardiac rhythm. By evaluating the morphology, IMD 12 may distinguish a 1:1 SVT from a 1:1 ventricular tachycardia having retrograde conduction.

Figure 2:
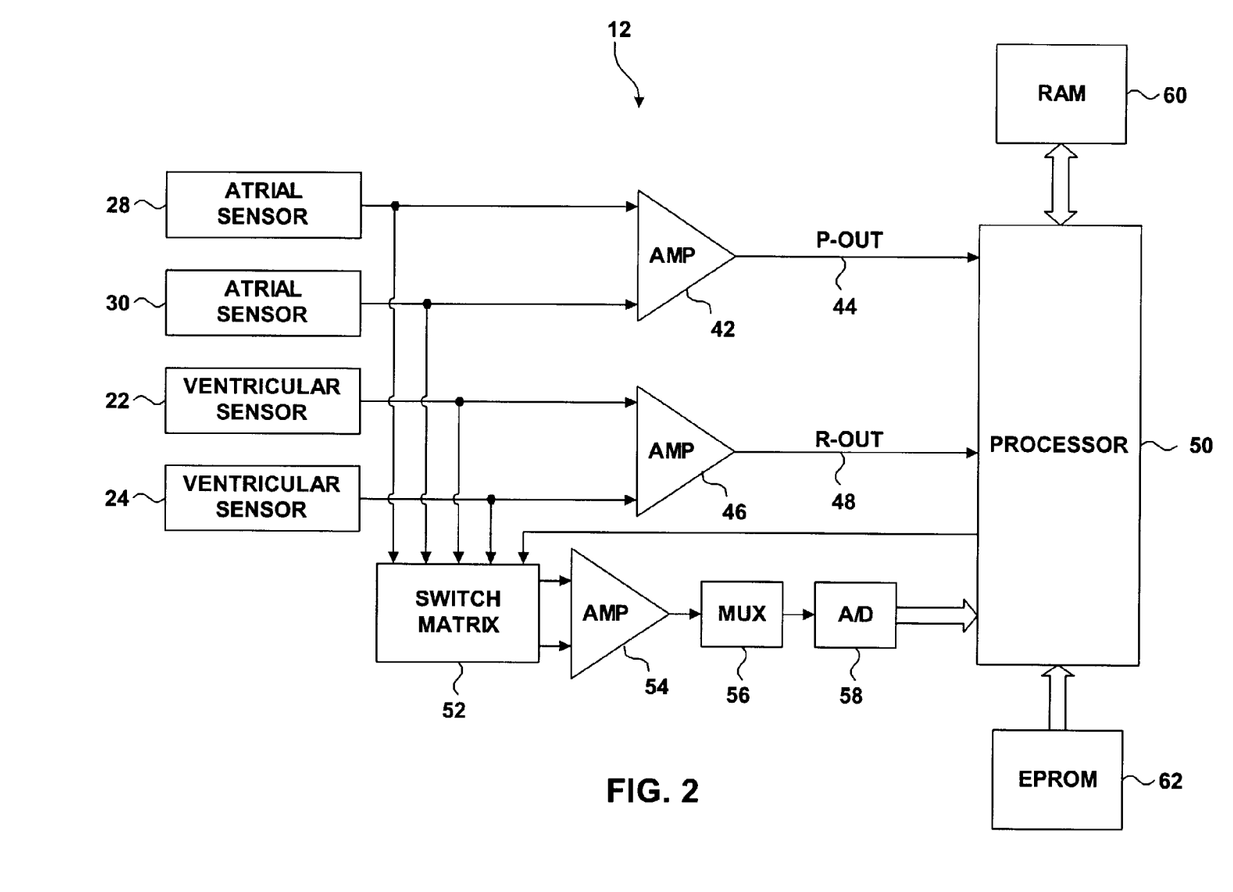
FIG. 2 is a block diagram illustrating example constituent components of the implantable medical device of FIG. 1.

FIG. 2 is a block diagram illustrating an example embodiment of IMD 12 (FIG. 1). More particularly, FIG. 2 is a block diagram illustrating one embodiment of the invention, in which IMD 12 is a microprocessor-based pacemaker. Although the techniques for discriminating SVTs with 1:1 AV conduction will be described in reference to a pacemaker, the techniques are not so limited. The techniques, for example, may be incorporated within other implanted medical devices, such as a pacemaker-cardioverter-defibrillator, an arrhythmia monitor that gathers data but does not provide any therapy to the patient, and the like.

IMD 12 receives atrial signals via atrial sense electrodes 28, 30, and receives ventricular signals via ventricular sense electrodes 22, 24. A sense amplifier 42 receives electrical signals from atrial sense electrodes 28, 30, amplifies and filters the signals, and senses whether the signals show an atrial activation. As used herein, an activation is defined as an electrical excitation that propagates along the cardiac tissue. Amplifier 42 may sense an atrial activation by techniques such as comparing the signal to a sense threshold. When amplifier 42 senses an atrial activation, amplifier 42 generates a digital signal on P-out line 44.

Similarly, a sense amplifier 46 receives signals from ventricular sense electrodes 22, 24, amplifies and filters the signals, and senses whether the signals show a ventricular activation. When amplifier 46 senses a ventricular activation, amplifier 46 generates a digital signal on R-out line 48.

Processor 50 receives the digital signals on P-out line 44 and the digital signals on R-out line 48. Processor 50 uses these signals to determine whether the patient has a fast heart rate, whether the heart rhythm exhibits evidence of sinus tachycardia and whether the heart rhythm exhibits 1:1 atrial to ventricular conduction. Techniques for evaluating whether the heart rhythm exhibits evidence of sinus tachycardia, and whether the heart rhythm exhibits 1:1 AV conduction, will be described in more detail herein.

Atrial sense electrodes 28, 30 and ventricular sense electrodes 22, 24 supply signals to switch matrix 52, which selects which of the available sensors are coupled to wide band (0.5 to 200 Hz) amplifier 54 for use in digital signal analysis. Processor 50 controls selection of sensors by switch matrix 52. Signals from the selected sensors are provided to multiplexer 56 and are converted to multi-bit digital signals by analog-to-digital (A/D) converter 58. The digital signals, which may include digital atrial waveforms, digital ventricular waveforms, or both, may be analyzed by processor 50. An atrial or ventricular waveform may be called an electrogram, or EGM.

Digital signal analysis of an EGM may include analysis of signal morphology. Morphological analysis may include, for example, wavelet analysis, Fourier analysis, signal correlation or template matching. In a typical application of the invention, processor 50 evaluates the morphology of a ventricular EGM. A normal morphology may indicate an SVT, while an abnormal morphology may indicate another kind of arrhythmia, such as ventricular tachycardia having retrograde conduction. For example, an electrical signal that follows an abnormal conduction path through heart 10 may exhibit a QRS complex that is shaped differently from a QRS complex that results from an electrical signal following the normal conduction path.

Morphological analysis algorithms may be encoded as a sequence of instructions stored in memory components such as random access memory (RAM) 60 or erasable programmable read-only memory (EPROM) 62, or any other combination of electronic storage elements. Processor 50 may load the instructions from RAM 60 or EPROM 62 when performing a morphological analysis.

RAM 60 or EPROM 62 may also store algorithms as sequences of instructions for determining whether system 40 should execute the instructions for performing a morphological analysis. For reasons that will be described below, morphological analysis will typically not be performed in every case, but will be reserved for hear rhythms that have passed other tests. In particular, morphological analysis may be reserved for heart rhythms in which the heart rate is rapid, evidence of sinus tachycardia is insufficient, and 1:1 AV conduction is exhibited. RAM 60 or EPROM 62 may store algorithms as sequences of instructions for determining whether the patient has a rapid heart rate, whether the heart rhythm is indicative of sinus tachycardia, and whether the heart rhythm exhibits 1:1 AV conduction.

The electronic components of IMD 12 may be powered by an internal power supply, such as a battery (not shown in FIG. 2). To prolong battery life, processor 50 may perform short-duration computations that use little energy. Computations to detect a rapid heart rate, to detect evidence of sinus tachycardia and to detect 1:1 AV conduction generally consume little energy. Computations involving morphological analysis, however, are generally more energy-demanding computations, and are performed when circumstances call for such morphological analysis.

Figure 3:
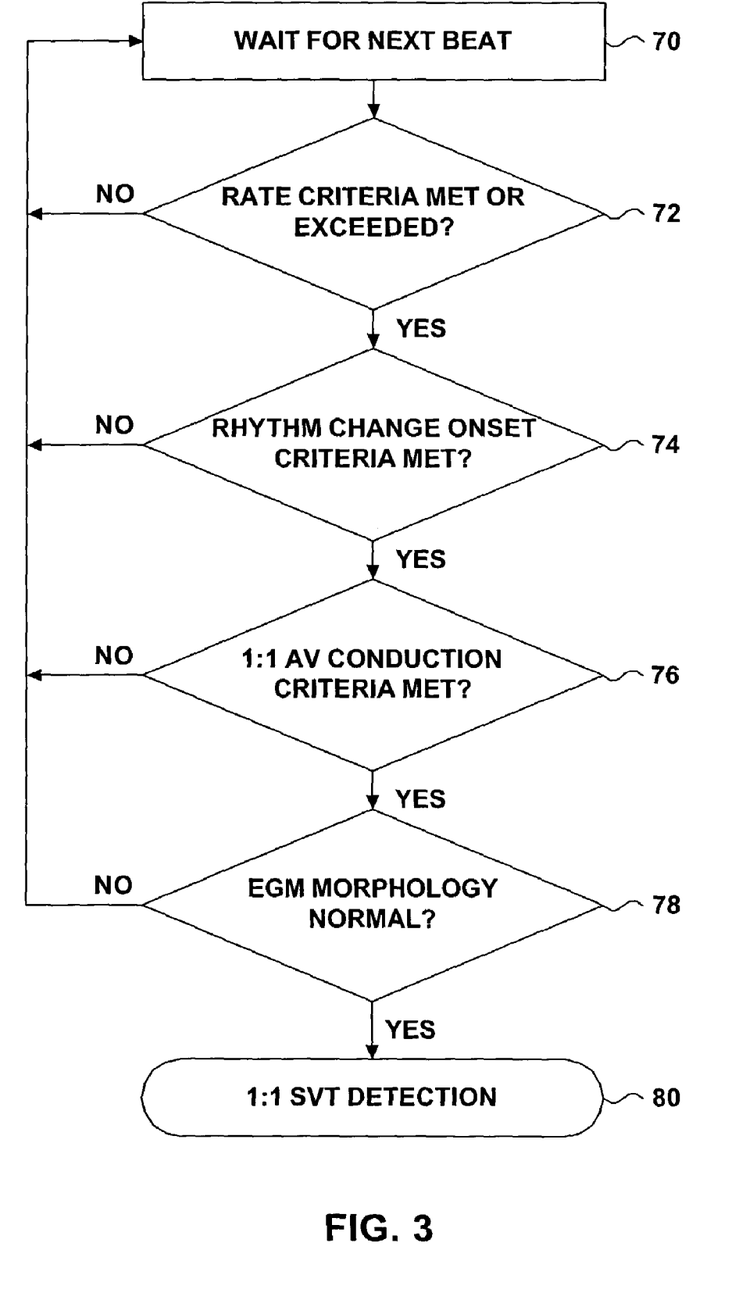
FIG. 3 is a flow diagram illustrating an example technique for discriminating an SVT with 1:1 AV conduction.

FIG. 3 is a flow diagram illustrating an example technique for discriminating SVTs with 1:1 AV conduction. As illustrated in FIG. 3, the technique involves the evaluation of whether a plurality of criteria have been satisfied. Although the technique is illustrated for exemplary purposes as sequential, the evaluations may be made sequentially, in parallel, or combinations thereof. Furthermore, the evaluations need not be applied in a particular order although, as described below, the order of application may be arranged to conserve computation resources.

Initially, processor 50 (FIG. 2) may analyze a heart rate of the patient on a beat-to-beat basis (70) and, for each beat, may determine whether the heart rate meets or exceeds fast heart rate criteria (72). Processor 50 may detect a fast heart rhythm by, for example, comparing a time interval between successive digital signals on R-out line 48 (FIG. 2) to a threshold time. When the interval between successive atrial activations is below the threshold time, for example, the heart rate may be deemed to be fast. Other techniques for detecting a fast heart rate may also be employed.

An SVT with 1:1 AV conduction is characterized by a rapid heart rate. A fast heart rate, however, is not necessarily caused by a 1:1 SVT. A fast heart rate may also be due to other forms of tachyarrhythmia, or may be due to sinus tachycardia in response to a physiological stimulus.

Processor 50 may evaluate the heart rhythm for changes (74). In particular, processor 50 may evaluate the heart rhythm for sudden change in a cardiac interval such as the time interval between successive R-waves (the R-R interval). Changes in heart rhythm may be evidence of sinus tachycardia, or may be indicative of one or more forms of tachyarrhythmia. A 1:1 SVT, along with some other forms of tachyarrhythmia, is characterized by abrupt changes in one or more cardiac intervals.

The R-R interval, for example, gradually shortens over several beats when the patient experiences sinus tachycardia, as the beats come closer and closer together in time. When the patient experiences a 1:1 SVT, by contrast, the onset of the rapid heart rate, and the shortened R-R intervals, is typically sudden. Accordingly, processor 50 may find evidence of sinus tachycardia when processor 50 observes a gradual onset of a fast heart rate. Processor 50 may apply any of several possible criteria for determining whether there has been a rapid or gradual onset of a fast heart rate Observation of a gradually shortening R-R interval is an exemplary test for heart rhythm changes, but is not the only possible test. Sinus tachycardia may be indicated or ruled out by other tests as well. For example, a change in the time interval between P-waves and R-waves (the P-R interval) may indicate that the heart is not in sinus tachycardia, but is experiencing some other form of tachyarrhythmia. A sudden change in the R-P interval likewise may be inconsistent with sinus tachycardia.

Whether sinus tachycardia is indicated or ruled out may be a matter of degree. Processor 50 may apply programmed standards to determine whether a change in a cardiac interval is a "sudden" change in the cardiac interval. Similarly, a heart rhythm may include some evidence of sinus tachycardia, and some evidence of a rhythm other than sinus tachycardia. Processor 50 may apply programmed standards to determine whether there is sufficient or insufficient evidence of sinus tachycardia. When the change in the cardiac interval is "sudden," or when there is insufficient evidence of sinus tachycardia, sinus tachycardia is deemed to be ruled out, and the rhythm change onset criteria may be deemed to have been met.

If the rhythm change onset criteria is met, processor 50 determines whether 1:1 AV conduction criteria is met (76). For example, processor 50 may test the heart rhythm for 1:1 atrial to ventricular conduction by comparing signals received on P-out line 44, which reflect the atrial rate, with signals received on R-out line 48, which reflect the ventricular rate. When the atrial rate exceeds the ventricular rate, then 1:1 AV conduction is not present.

In some applications of the invention, processor 50 may test the heart rhythm for substantially 1:1 atrial to ventricular conduction. Strict one-to-one correspondence of atrial and ventricular activations is not required for a determination that 1:1 AV conduction is present. For example, processor 50 may determine that seven ventricular activations for every eight atrial activations qualifies as substantially 1:1 AV conduction, or processor 50 may determine that substantially 1:1 AV conduction is present when the median atrial rate is approximately equal to the median ventricular rate, plus or minus a programmed error range.

The absence of 1:1 AV conduction may rule out the possibility of a 1:1 SVT, but the presence of 1:1 AV conduction still does not establish a 1:1 SVT. Some forms of ventricular tachycardia exhibit 1:1 retrograde conduction. The EGM accompanying these ventricular tachyarrhythmias, however, exhibits an abnormal morphology. The EGM accompanying an SVT, by contrast, follows a normal signal conduction path through heart 10 and produces an EGM that exhibits a normal morphology.

Accordingly, processor 50 may direct switch matrix 52 to select one or more EGM signals, such as ventricular EGM from ventricular sensor 22 or 24, for a morphological analysis to determine whether the EGM morphology is "normal," as further described below (78). The EGM signal may be sampled by A/D converter 58 and converted to a digital signal for analysis. As noted above, morphological analysis may include any of several techniques, such as wavelet analysis, Fourier analysis, signal correlation or template matching. The satisfaction of the other criteria, and a normal morphology, indicates a 1:1 SVT (80), while an abnormal morphology indicates another form of tachyarrhythmia.

Processor 50 may perform a morphological analysis for several cardiac cycles. For example, processor 50 may analyze the morphology for eight cardiac cycles. Furthermore, processor 50 may determine that the EGM is abnormal when a programmed number of cardiac cycles, such as three of the eight analyzed cycles, exhibit an abnormal morphology.

In the embodiment of the invention shown in FIG. 3, morphological analysis is reserved as the final step in discriminating a 1:1 SVT, and is not employed unless other tests have failed to rule out a 1:1 SVT. Morphological analysis often involves powerful and relatively complicated analysis algorithms, and consequently involves extensive computation by processor 50. As a result, morphological analysis may take more computing resources than the other tests, and may therefore consume more energy than many other operations of processor 50. To preserve battery life, morphological analysis may be avoided when a 1:1 SVT has been ruled out by other tests. The invention encompasses embodiments, however, in which morphological analysis is performed at another stage, or in parallel with the other test.

Figure 4:
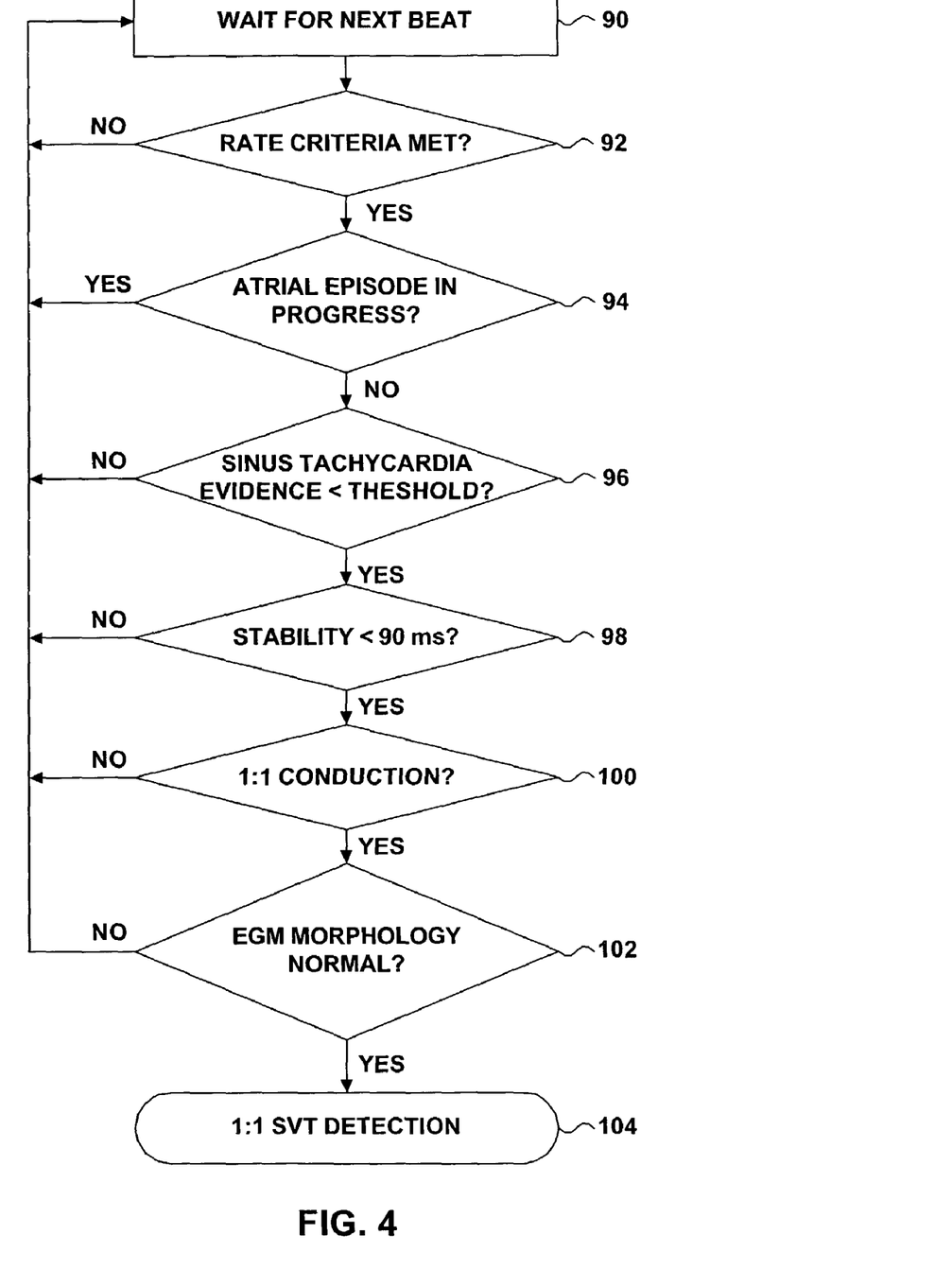
FIG. 4 is a flow diagram illustrating implementation of the technique in FIG. 3 with exemplary discriminatory algorithms.

FIG. 4 is a flow diagram illustrating an example implementation of the techniques shown in FIG. 3. In particular, FIG. 4 illustrates use of discriminatory algorithms to perform the operations shown in FIG. 3. These discriminatory algorithms may be performed by an IMD to discriminate among the various forms of arrhythmia. The techniques of FIG. 4, therefore, illustrate how a 1:1 SVT may be detected when the IMD applies algorithms to detect other forms of arrhythmia.

As in FIG. 3, processor 50 may analyze the heart rate on a beat-to-beat basis (90) and may determine whether the heart rate meets or exceeds the fast heart rate criteria (92). When a fast heart rate is detected, a 1:1 SVT may be in progress, but sinus tachycardia or another tachyarrhythmia may also be in progress.

Next, processor 50 may analyze whether an atrial episode is in progress (94). Many implanted medical devices include an algorithm for determining whether an atrial episode such as atrial fibrillation or atrial flutter is in progress. Atrial episodes are characterized by >1:1 AV conduction. Therefore, when such an atrial episode is in progress, 1:1 SVT is not present. Processor 50 may determine that an atrial episode is in progress by, for example, counting the number of atrial events and ventricular events that take place per a number of beats or an interval of time and determining whether the atrial events substantially outnumber the ventricular events.

Processor 50 may evaluate the heart rhythm for evidence of sinus tachycardia (96). As noted above, processor 50 may look for changes in the heart rhythm, such as abrupt shortening of the R-R interval or a sudden change in the P-R interval. Processor 50 may also rule out sinus tachycardia when AV conduction is other than 1:1. In some IMDs, processor 50 employs an algorithm in which evidence of sinus tachycardia is counted over a programmed duration, and the counted evidence is compared to a threshold. In such devices, processor 50 determines that sinus tachycardia is present when the evidence of sinus tachycardia exceeds the threshold. When the evidence of sinus tachycardia is below the threshold, there is insufficient evidence of sinus tachycardia, and sinus tachycardia is deemed not to be present.

After sinus tachycardia is ruled out, processor 50 may employ an algorithm to test the heart rhythm for stability (98). A 1:1 SVT is stable from beat to beat, but other rhythms are not stable. For example, bigeminy, in which a premature ventricular contraction follows a normal ventricular activation, is usually not stable from beat to beat, but is evidenced by variations in the R-R interval. When consecutive R-R intervals differ by more than 90 milliseconds, for example, bigeminy may be indicated.

Processor 50 may execute an algorithm to eliminate the possibility of <1:1 AV conduction (100), in which the ventricle activates more frequently than the atrium. When the rhythm passes the above tests, processor 50 may perform a morphological analysis (102) of an EGM signal as described above. A normal morphology indicates an SVT with 1:1 AV conduction (104).

The invention may offer one or more advantages. By identifying 1:1 SVTs, appropriate therapy may be provided for this form of arrhythmia. In addition, therapy that may be risky for 1:1 SVTs may be avoided. Furthermore, the techniques for discriminating SVTs with 1:1 AV conduction can operate harmoniously with techniques for discriminating other arrhythmias. In particular, an implanted medical device may be able to distinguish a 1:1 SVT from a >1:1 SVT.

Various embodiments of the invention have been described. The preceding specific embodiments are illustrative of the practice of the invention. Various modifications may be made without departing from the scope of the claims. For example, the invention is not limited to the techniques shown in FIGS. 3 and 4. The order in which tests are performed need not be exactly the same as shown in FIGS. 3 and 4, for example, and in some circumstances, several tests may be combined or performed simultaneously.

The invention may be embodied in a computer-readable medium with instructions that cause a programmable processor to carry out the techniques described above. A "computer-readable medium" includes but is not limited to read-only memory, Flash memory, EPROM and a magnetic or optical storage medium. The medium may comprise instructions for causing a programmable processor to determine that a cardiac rhythm indicates an SVT with 1:1 AV conduction when the rhythm exhibits insufficient evidence of sinus tachycardia, the rhythm exhibits 1:1 conduction, and an electrical signal corresponding to the cardiac rhythm exhibits a normal morphology. These and other embodiments are within the scope of the following claims.

What is claimed is:

1. A method comprising:
   sensing a cardiac rhythm;
   determining whether a first rate corresponding to the sensed cardiac rhythm is greater than a first predetermined threshold;
   determining whether a second rate corresponding to an onset of the sensed cardiac rhythm is greater than a second predetermined threshold; and
   determining, in response to the first rate being greater than the first predetermined threshold and the second rate being greater than the second threshold, whether the sensed cardiac rhythm indicates a supraventricular tachycardia (SVT) with 1:1 atrial to ventricular conduction (1:1 AV conduction).

2. The method of claim 1, further comprising:
   determining, in response to the sensed cardiac rhythm indicating an SVT with 1:1 AV conduction, whether a morphology of the sensed cardiac rhythm corresponds to a predetermined morphology; and
   verifying the indication of an SVT with 1:1 AV conduction in response to the morphology corresponding to the predetermined morphology.

3. The method of claim 2, wherein determining whether a morphology of the sensed cardiac rhythm comprises one of a wavelet analysis, a Fourier analysis, a signal correlation and a template matching.

4. A computer-readable medium comprising instructions for causing a programmable processor to:
   sense a cardiac rhythm;
   determine whether a first rate corresponding to the sense cardiac rhythm is greater than a first predetermined threshold;
   determine whether a second rate corresponding to an onset of the sensed cardiac rhythm is greater than a second predetermined threshold; and
   determine, in response to the first rate being greater than the first predetermined threshold and the second rate being greater than the second threshold, whether the sensed cardiac rhythm indicates a supraventricular tachycardia (SVT) with 1:1 atrial to ventricular conduction (1:1 AV conduction).

5. The medium of claim 4, the instructions further causing the processor to determine, in response to the sensed cardiac rhythm indicating an SVT with 1:1 AV conduction, whether a morphology of the sensed cardiac rhythm corresponds to a predetermined morphology; and to verify the indication of an SVT with 1:1 AV conduction in response to the morphology corresponding to the predetermined morphology.

6. The medium of claim 5, wherein the instructions causing the processor to determine whether a morphology of the sensed cardiac rhythm corresponds to a predetermined morphology cause the processor to perform at least one of a wavelet analysis, a Fourier analysis, a signal correlation and a template matching.

7. A medical device comprising:
   a sensor proximate to a heart sensing cardiac signals; a processor determining whether a first rate corresponding to the sensed cardiac signals is greater than a first predetermined threshold, whether a second rate corresponding to an onset of the sensed cardiac signals is greater than a second predetermined threshold, and wherein the processor determines, in response to the first rate being greater than the first predetermined threshold and the second rate being greater than the second threshold, whether the sensed cardiac signals indicate an SVT with 1:1 AV conduction.

8. The device of claim 7, wherein the processor determines, in response to the sensed cardiac signals indicating an SVT with 1:1 AV conduction, whether a morphology of the sensed cardiac signals corresponds to a predetermined morphology, and verifies the indication of an SVT with 1:1 AV conduction in response to the morphology corresponding to the predetermined morphology.

9. The device of claim 8, further comprising:
a sense amplifier that receives an electrical signal corresponding to the sensed cardiac signals and generates an activation signal as a function of the electrical signal; and
an analog-to-digital converter that receives the electrical signal and generates an digital electrogram signal as a function of the electrical signal.

10. The device of claim 9, wherein the processor analyzes the morphology of the electrical signal corresponding to the cardiac rhythm by analyzing the morphology of the digital electrogram signal.

11. The device of claim 7, wherein the sensor is a first sensor proximate to a ventricle of the heart, the device further comprising a second sensor proximate to an atrium of the heart.

12. The device of claim 7, wherein the device is implantable in a human body.

* * * * *

UNITED STATES PATENT AND TRADEMARK OFFICE
CERTIFICATE OF CORRECTION

PATENT NO. : 6,980,860 B2  
APPLICATION NO. : 10/284874  
DATED : December 27, 2005  
INVENTOR(S) : Robert W. Stadler et al.

Page 1 of 1

It is certified that error appears in the above-identified patent and that said Letters Patent is hereby corrected as shown below:

Claim 4, Col. 8, lines 28 - 29, delete "to the sense cardiac rhythm"

and insert in place thereof -- to the sensed cardiac rhythm --.

Signed and Sealed this

Twenty-fourth Day of February, 2009

JOHN DOLL  
*Acting Director of the United States Patent and Trademark Office*